United States Patent [19]
Liston et al.

[11] Patent Number: 5,357,113
[45] Date of Patent: Oct. 18, 1994

[54] INFRARED GAS MIXTURE ANALYZER

[75] Inventors: Max D. Liston, Irvine; Todd I. Harrison, Santa Ana; Paul K. Hsei, Huntington Beach; Wayne F. Blackburn, Irvine, all of Calif.

[73] Assignee: Liston Scientific Corp., Irvine, Calif.

[21] Appl. No.: 977,662

[22] Filed: Nov. 18, 1992

[51] Int. Cl.5 ............................................. G01N 21/37
[52] U.S. Cl. ................................... 250/344; 250/343
[58] Field of Search ................. 250/343, 344; 356/437

[56] References Cited

U.S. PATENT DOCUMENTS

| | | |
|---|---|---|
| 2,573,870 | 11/1951 | Pfund . |
| 2,698,390 | 12/1954 | Liston . |
| 3,105,147 | 9/1963 | Weilbach et al. . |
| 3,130,302 | 4/1964 | Liston et al. . |
| 3,215,832 | 11/1965 | Madsen . |
| 3,227,873 | 1/1966 | Liston . |
| 3,745,348 | 7/1973 | Kummeke . |
| 4,420,690 | 12/1983 | Kuehl .......................... 250/343 X |
| 4,525,069 | 6/1985 | Tanaka et al. ................ 356/435 |
| 4,557,603 | 12/1985 | Oehler et al. ................. 250/343 X |
| 4,581,714 | 4/1986 | Reid ............................ 364/571 |
| 4,692,622 | 9/1987 | Taniguchi et al. ............ 250/344 X |
| 4,742,229 | 5/1988 | Weinel ......................... 250/344 X |
| 5,055,690 | 10/1991 | Bonne ......................... 250/339 X |

FOREIGN PATENT DOCUMENTS

| | | | |
|---|---|---|---|
| 2341857 | 9/1977 | France ......................... | 250/344 |
| 1188626 | 4/1970 | United Kingdom ............. | 250/344 |

*Primary Examiner*—Constantine Hannaher
*Assistant Examiner*—Edward J. Glick
*Attorney, Agent, or Firm*—Stetina and Brunda

[57] ABSTRACT

A pneumatic detector, non-dispersive infrared analyzer employing detector cell chambers in optical series. The invention having an auxiliary chamber communicating with the front chamber to increase the rear chamber's signal so as to balance the signals from the front and rear chambers. The use of xenon as a diluent gas in the detector chambers in combination with a mass flow detector to improve the sensitivity. The use of an improved synchronous detection method employing a voltage-to-frequency circuit to convert the detector signal to a synchronous high resolution digital signal. The use of an improved source electrically pulsed having low thermal mass and a large radiating area.

14 Claims, 3 Drawing Sheets

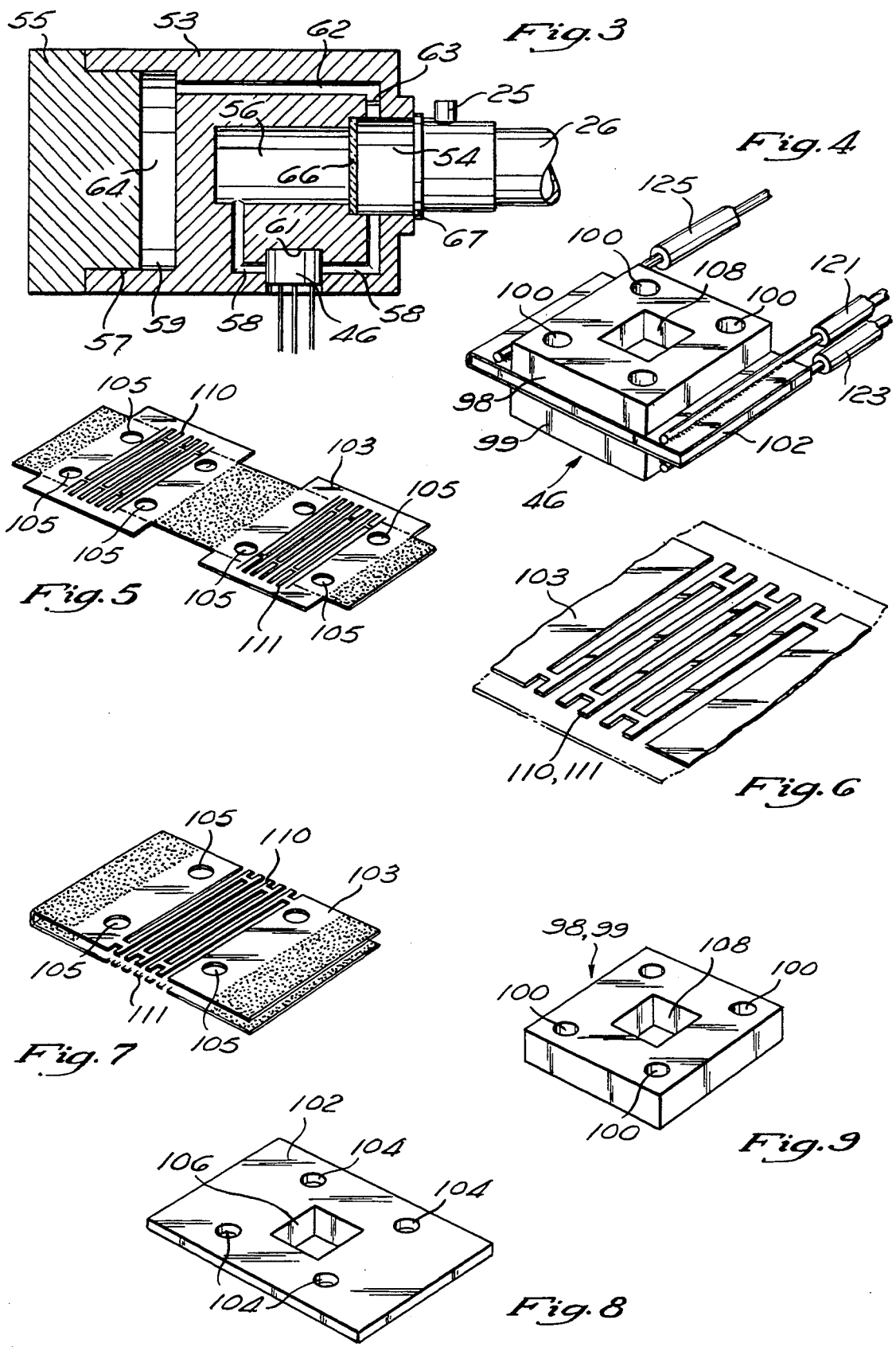

INFRARED GAS MIXTURE ANALYZER

FIELD OF THE INVENTION

The present invention relates generally to gas detection devices and more particularly to an infrared analyzer utilizing optically seriesed detection cells employing detection chambers in optical series together with a balancing chamber to detect the presence of various dipole gases such as carbon monoxide (CO), carbon dioxide ($CO_2$), water vapor, $SO_2$, $CH_4$, etc.

BACKGROUND OF THE INVENTION

As is well-known, certain gases can be measured both qualitatively and quantitatively by means of infrared radiation absorption wherein a detector cell, typically containing a quantity of the same gas as that desired to be measured, utilizes a sensor to measure thermal expansion of the gas within the detector cell induced by the absorption of the infrared radiation. The gas to be analyzed is typically contained within a sample cell such that it attenuates the infrared radiation prior to the infrared radiation entering the detector cell. The particular wavelength and amount of infrared radiation absorbed by the gas within the detector cell provides an indication of the type of gas present in the sample cell and the quantity thereof, since such absorption is a function of the attenuation occurring in the sample cell.

Numerous prior art infrared gas detection devices have been developed which are generally known as pneumatic detector analyzers. Such prior art pneumatic analyzers have the ability to analyze a gas of interest in the presence of other interfering gases having overlapping infrared spectrums. In such pneumatic analyzers, the selectivity of the analyzer is attained by using the gas to be analyzed in the detector to make the detector sensitive to the same.

The vast majority of the early prior art non-dispersive infrared analyzer devices employing pneumatic detection techniques utilized two separate radiation beams wherein the unknown gas sample was passed through the first beam and a second beam as employed to produce a balancing effect. Examples of such dual-beam systems are found in U.S. Pat. No. 2,573,870, issued to Pfund and U.S. Pat. No. 2,698,390, issued to Liston, one of the co-inventors of the subject application.

Such dual-beam detection techniques possessed the advantage of reducing the adverse effects of encountering small changes in source emissions, detector sensitivity, and amplifier gain and produced a signal which had a larger effective change due to the presence of the gas desired to be analyzed- However, the compensation for source emission changes was not sufficient in such prior art devices due to the dual beams not having identical views of the radiation source. Further, changes in the optical transmission of the dual beams also produced an undesirable signal drift; for example, a very slight accumulation of dirt or debris in the sample cell of such prior art dual beam systems would produce a significant zero shift in the detector signal.

Subsequently, pneumatic detector infrared gas analyzers were developed employing a single radiation beam utilizing either dual detectors or dual radiation sources. Example of such single-beam pneumatic analyzers utilizing dual detectors are found in U.S. Pat. No. 3,105,147, issued to Weilbach et al. and U.S. Pat. No. 3,130,302, issued to Liston et al, while an example of single-beam pneumatic analyzers utilizing dual radiation sources is found in U.S. Pat. No. 3,227,873, additionally issued to Liston. Such prior art single-beam instruments had the advantage that the radiation source was viewed through an identical optical path by the detectors with the second detector of the dual detectors additionally affording a means to compensate for interference from other compounds found in the gas sample. The prior art single-beam dual detector instruments had the advantage that compensation for changes in the source radiation and/or sample cell was excellent. However, such prior art analyzers had the significant disadvantage that differences in temperature coefficients of the dual sensors produced a significant signal drift. Further, such dual sensor devices proved to be significantly expensive to produce.

Most recently, infrared gas analyzers employing a pneumatic detection technique have been developed employing a dual chamber formed in optical series with a single sensing element or detector. The use of such optical series detector chambers provide a common optical path which reduces the effects in transmission of the sample cell and source emission. It also reduces the effect of changes in the detector sensor sensitivity. However, this compensation is incomplete since the signal from the front detector chamber is always stronger. This difference in signal was due to the fact that the infrared radiation was substantially attenuated by the gas contained within the front detection cell and thus did not affect the rear detection cell to the same degree.

By balancing the signals from the front and rear detector chambers these adverse effects are eliminated since a change in the energy entering the detector does not change the signal output. The closer to balance the less the effect of these variables.

The adverse effect of signal strength difference in the front and rear chambers is of particular concern in prior art infrared analyzers utilizing the mass flow of gas as a means of measuring infrared radiation absorption. In such prior art infrared analyzers, gas flow through a conduit interconnecting the front and rear detection cells is measured to provide an indication of infrared absorption in the two detection cells. If the front detection cell's optical path is reduced in an effort to achieve balance, then the volume that is available for the gas flow from the second detection cell is restricted by the buildup of pressure in the first detection cell, thus reducing the signal from the second detection cell and defeating the attempt to balance the signals.

Thus, there exists a substantial need in the art to provide an optically seriesed detector infrared analyzer in which the signals from the front and rear detection cells are balanced and which does not suffer from restriction of gas flow due to the buildup of pressure in the first detection cell.

Additionally, $N_2$ has been typically employed as a diluent gas in contemporary pneumatic detector infrared analyzers. The diluent gas is that gas which is mixed with the gas of interest and generally used to charge at least one of the two detector cells. Since it is the gas expansion or flow produced by the selective absorption of infrared radiation by the sensitizing gas which is measured by the sensor, it is thus desirable to minimize any counteracting effects of the diluent gas. The thermal conduction of the diluent gas determines the rate at which heat absorbed by the sensitizing gas is conducted to the walls of the cell. Thus, there exists a need in the art to use a diluent gas having minimal thermal conduction.

Furthermore, when employing a mass flow sensor, a diluent gas with low specific heat gives a much larger signal for the same amount of thermal energy. Therefore, it would similarly be desirable to utilize a diluent gas having the lowest specific heat.

In an analyzer where operation is near or at balance, synchronous detection of the detector signal is required to avoid confusion as to which side of balance the system is. High accuracy and resolution is required to prevent degrading the system. Previous analyzers have employed synchronous switching of the analog signal for this purpose. A high resolution analog-to-digital converter is required to convert this rectified signal for processing by modern microprocessors. In the invention a voltage-to-frequency converter circuit is employed using the counter in the microprocessor for this purpose. This voltage-to-frequency circuit is much cheaper and more accurate.

SUMMARY OF THE INVENTION

The present invention specifically addresses and alleviates the above-referenced deficiencies associated in the prior art by providing an optically seriesed detector infrared analyzer having a front detector chamber; a rear detector chamber with a window separating the front and rear detector chambers; and a balancing chamber connected to the front chamber whose size is designed to equalize the signals as sensed by a mass flow detector connected by conducts between the front and back chambers. The gas to be analyzed is disposed within a sample cell having a reflective surface preferably formed of a film comprised of gold deposited upon its interior to minimize the loss of infrared radiation by absorption into the sample cells's wall. A pulsed infrared radiation source is utilized having a low thermal mass element and a large radiating area. Although numerous diluent gases are contemplated, in the preferred embodiment xenon gas is utilized as a diluent gas in the detector cells to minimize thermal conduction and specific heat. Further, digital look-up tables are preferably utilized to effect accurate real-time linearization of the infrared analyzer output.

The infrared analyzer of the present invention is particularly suitable for use in such applications as monitoring the CO concentration in the exhaust gases associated with various industrial processes such as vehicular and smoke stack emissions. Those skilled in the art will recognize however that numerous other applications exist which are clearly contemplated in the spirit of the present invention.

The novel auxiliary or balancing chamber of the present invention is in fluid communication with the front detector chamber to control the flow or pressure from the first and back chambers. Furthermore, by adjusting the volumetric size of the balancing chamber to equalize the generated detector signals from the front and back chambers, instability of the infrared radiation source and optical system can be minimized. Thus, by sizing the optical path of the front detector cell less than that of the rear detector cell, and by utilizing the volume of the auxiliary balancing chamber to facilitate gas flow from the second detector cell into the first detector cell, balancing of the signals from the two detector cells can be attained. Since the flow signals from the front and rear chambers are not 180 degrees apart due to the differences in thermal conduction and flow restriction, the front or rear chamber signals can be favored by phasing correct for either the front or rear signals. This can be employed to reduce the response to an interfering gas in the sample.

In the preferred embodiment, the size of the balancing chamber is empirically designed so that the signals from the two detection cells or chambers are essentially in balance during zero concentration conditions of the unknown analyte. This condition provides the best compensation for changes in source and sample cell transmission. This balanced condition also tends to give better compensation from interfering compounds that have overlapping absorption bands. In order to operate at this preferred balanced condition, it is necessary to employ phase detection of the AC signal to avoid confusion as the balance goes through zero.

The use of xenon as a diluent gas in the present invention is preferred over other possible monatomic gases, such as $O_2$ and $N_2$, and other rare gases due to its superior thermal conduction and specific heat properties. The table below illustrates a comparison of the thermal conduction and specific heats of such principal candidate gases.

| GAS | THERMAL CONDUCTION (cal/sec/cm$^2$) $\times 10^{-6}$ | SPECIFIC HEAT |
| --- | --- | --- |
| $N_2$ | 58 | .249 |
| $O_2$ | 59 | .219 |
| Argon | 52 | .124 |
| Neon | 108 | .246 |
| Xenon | 13.6 | .0346 |
| Krypton | 22.4 | .059 |

A comparison of the thermal conduction and specific heat properties of the above-listed gases shows xenon to be superior in these respects. By utilizing a detector with a charge of 10 percent CO in xenon versus 10 percent CO in $N_2$, an improvement in signal sensitivity of approximately three times is realized.

Thus, in the preferred embodiment of the present invention, xenon gas is utilized as the diluent gas within the front and rear detection cells. A sensitizing gas is mixed with the xenon gas. The sensitizing gas has substantially similar infrared absorption spectra to that of the gas being analyzed.

The present invention additionally incorporates a unique mass flow sensor which is formed in a novel methodology to provide extremely accurate sensor measurements. In the preferred embodiment, this sensor element is formed of an extremely thin strip of titanium which is subsequently photo-etched to provide a pair of titanium grids with the grid elements being subsequently trimmed to provide a series electrical connection therebetween. Opposite end portions and the central portion of the titanium strip are selectively coated by a sputtering technique with a thin layer of chromium, nickel, and copper. The opposite end portions and the central portion may then be utilized to receive conventional electrical leads, affixed by conventional silver solder techniques, with the central portion comprising a common lead connector and the opposite end portions providing separate lead connectors for ultimate connection to the amplifier circuitry of the invention. The titanium strip is then folded over upon itself such that the pair of resistive heating element titanium grids are axially aligned and are separated from one another by a glass spacer. The resultant sensor element is then positioned within a flow conduit existing between the first and second detection cells wherein the respective titanium grids generate an electric signal dependent upon the amount of cooling of the grid associated with mass flow of the gas thereacross.

The use of a pulsed source in the present invention eliminates the gas heretofore present in the optical path necessary to accommodate the light shutter and motor, thereby eliminating absorption errors caused by ambient air and/or contaminants in the shutter gap. The pulsed infrared radiation source of the present invention preferably comprises a radiation element formed of an extremely thin foil strip, preferably less than 0.000508 centimeters (0.0002 inch) thick, disposed within a V-shaped reflector. It has been found that a nickel aluminum alloy, such as KANTHAL, is a preferred material candidate, however, a platinum-tungsten alloy containing approximately 10 percent tungsten may additionally be used for the radiation element. To improve the emission of the radiation element, a thin layer of nickel is sputtered onto the foil when platinum tungsten alloy is utilized. Such nickel coating is then oxidized to produce a surface which exhibits excellent good black body emission in the infrared band.

An infrared window, preferably formed of sapphire, is additionally employed to seal the radiation source. The source is then preferably hard vacuumed in the presence of a desiccant to remove contaminants, such as water vapor, therefrom and the sapphire window is coated with a filter material to eliminate any water signal passing through the window. Alternatively the source may be charged with any interfering gases or vapors expected to be present in the sample gas to further reduce the system's response to these gases. Since the source case is hot, interfering vapors can be contained at higher concentration than is possible when a contemporary gas filter is employed. The heat of the source prevents condensation of the interfering vapors on the inner walls of the source.

As opposed to conventional prior art infrared analyzers which employ an analog-to-digital conversion of sensor output, the present invention instead utilizes a novel voltage-to-frequency conversion circuit. Such a voltage-to-frequency conversion circuit enables synchronous conversion of the AC signal generated by the sensor element to a digital signal which enables synchronous conversion of the AC signal to a digital signal with extremely high resolution and better response than conventional circuits.

In operation of the present invention, a gas is analyzed by disposing a sample of the gas to be analyzed in the sample cell. The gas is then radiated with infrared radiation from the pulsed infrared radiation source. A portion of the infrared radiation from the pulsed infrared radiation source is absorbed by the dipole gas being analyzed which is disposed within the sample cell. The amount of infrared radiation absorbed is dependent upon the amount of gas present and the wavelength of infrared radiation absorbed is dependent upon the particular gas being analyzed. The particular wavelength of infrared radiation being absorbed can be determined by filtering the infrared radiation from the source prior to its entering the sample cell and observing the effect upon the detector.

That portion of the infrared radiation which is not absorbed by the gas in the sample cell is transmitted therethrough to the front detection cell of the detector wherein it is partially absorbed and thereby causes expansion of the gas within the front detection cell. That portion of the infrared radiation which is not absorbed by the gas within the front detection cell is transmitted therethrough to the rear detection cell wherein a further portion of the infrared radiation is absorbed.

The pulsed operation of the infrared radiation source causes alternating expansion and contraction of the gases within the front and rear detection cells. The front and rear detection cells are connected via a conduit having the flow sensor mounted therein such that flow of gas through the conduit can accurately be measured. The amount of flow through the conduit is inversely proportional to the concentration of the gas being analyzed. Flow through the conduit is directly proportional to the absorption of infrared radiation by the gases contained within the front and rear detector cells and the consequent expansion of these gases.

The volume of the auxiliary chamber, which is in fluid communication with the front detection cell, is empirically chosen such that zero flow occurs when no dipole gas is present in the sample cell. This provides a balanced condition which compensates for the presence of any interfering gases.

With the introduction of a dipole gas into the sample cell, a portion of the infrared radiation passing therethrough is absorbed and thus changes the amount of infrared radiation reaching the front and rear detection cells of the detector. Reduction in the amount of infrared radiation reaching the first and second chambers of the detector results in an imbalanced condition wherein pressure differences between the front and rear detection cells result in the flow of gas through the interconnecting conduit which is measured by the flow sensor. The amount of flow is proportional to the amount of infrared radiation absorbed by the gas in the sample cell and therefore provides an indication of the concentration of the gas being analyzed.

The dual-resistive heater type flow sensor utilized in the present invention is heated by current flow therethrough and is disposed within the interconnecting conduit between the front and rear detection cells. The flow of gas over the pair of heated elements results in cooling thereof, thereby lowering the resistance of the elements. The resistance of the elements is therefore inversely proportional to the flow of gas thereover. By utilizing dual-heated elements at different positions along the interconnecting conduit, the direction of flow can be determined since cooling of the elements will be effected at different times. A differential amplifier is preferably utilized to provide a signal which is proportional to the flow rate. The phase of the output of the differential amplifies is proportional to the direction of the gas flow.

The output of the flow sensor comprises an AC signal due to the periodic nature of the gas flow through the conduit. The AC output is amplified to boost the signal to a suitable level for conversion to a corresponding DC signal. This rectification is preferably performed in synchronism with the source chopping to provide a superior signal-to-noise ratio and to avoid errors due to the reversal of phase on balanced systems.

To provide fast response for the analyzer, it is necessary to chop the source at a high frequency. Since infrared detectors have inherently poor frequency response, a compromise between system response time and signal-to-noise ratio is necessary. A voltage-to-frequency circuit integrates the signal over a cycle, i.e. a reversal of phase due to the reversal of gas flow in the conduit. Thus, the use of a voltage-to-frequency circuit eliminates the need for the low pass filters required between the detector and the analog-to-digital converter in contemporary methodologies.

The signal is communicated to the voltage-to-frequency converter. The output of the voltage-to-frequency converter is provided to a circuit counter wherein a processor, preferably a microprocessor, counts the pulses for the positive half of the source signal, and subtracts the signal during the second half. The timing or phasing on when to add and subtract is adjusted by an 8-bit switch instructing the microprocessor. In addition to enabling adjustment for differences in response times of the flow sensor, source, etc., this switch enables adjustment to reduce unwanted response to interfering gases. The difference is a measure of the integrated signal during the cycle which is the equivalent of an analog-to-digital conversion with 16-place accuracy. This integrated reading can be used as a new value for providing a current update every cycle. Where fast response is not required, a weighted averaging is employed to remove the noise at the expense of speed of response.

A reduction of this compromise may be obtained by varying the weighting according to the magnitude of the change. For example, for changes less than 25 percent of full scale, no averaging is employed and for changes less than one percent, a maximum weighting is utilized. Thus, the infrared analyzer of the present invention provides an inexpensive method of synchronous detection of an AC signal and conversion to digital form with better than 16-bit accuracy. Improved overall system response is obtained utilizing low-chop energy chopping rates.

These, as well as other advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 3 is an enlarged cross-sectional view of the detector of FIGS. 1 and 2;

FIG. 4 is an enlarged perspective view of the mass flow sensor of FIG. 3;

FIG. 5 is an enlarged perspective view of the titanium strip depicting the manner in which the pair of grid elements is formed thereon;

FIG. 6 is an enlarged perspective view of one of the pair of grid elements of FIG. 5;

FIG. 7 illustrates the manner in which the titanium strip is folded over upon itself to provide a pair of spaced grid elements;

FIG. 8 is a perspective view of the spacer element which is sandwiched between the grid elements;

FIG. 9 is a perspective view of one of the pair of mounting plates utilized in assembly of the mass flow sensor;

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
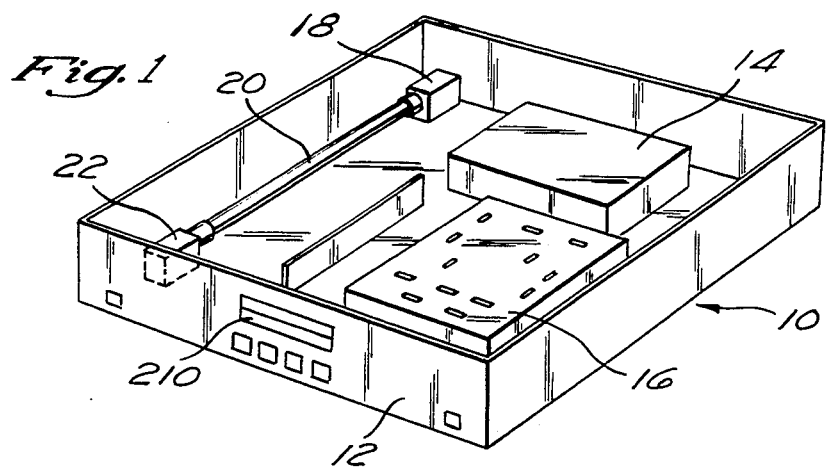
FIG. 1 is a perspective view of the infrared gas mixture analyzer of the present invention.
Figure 2:
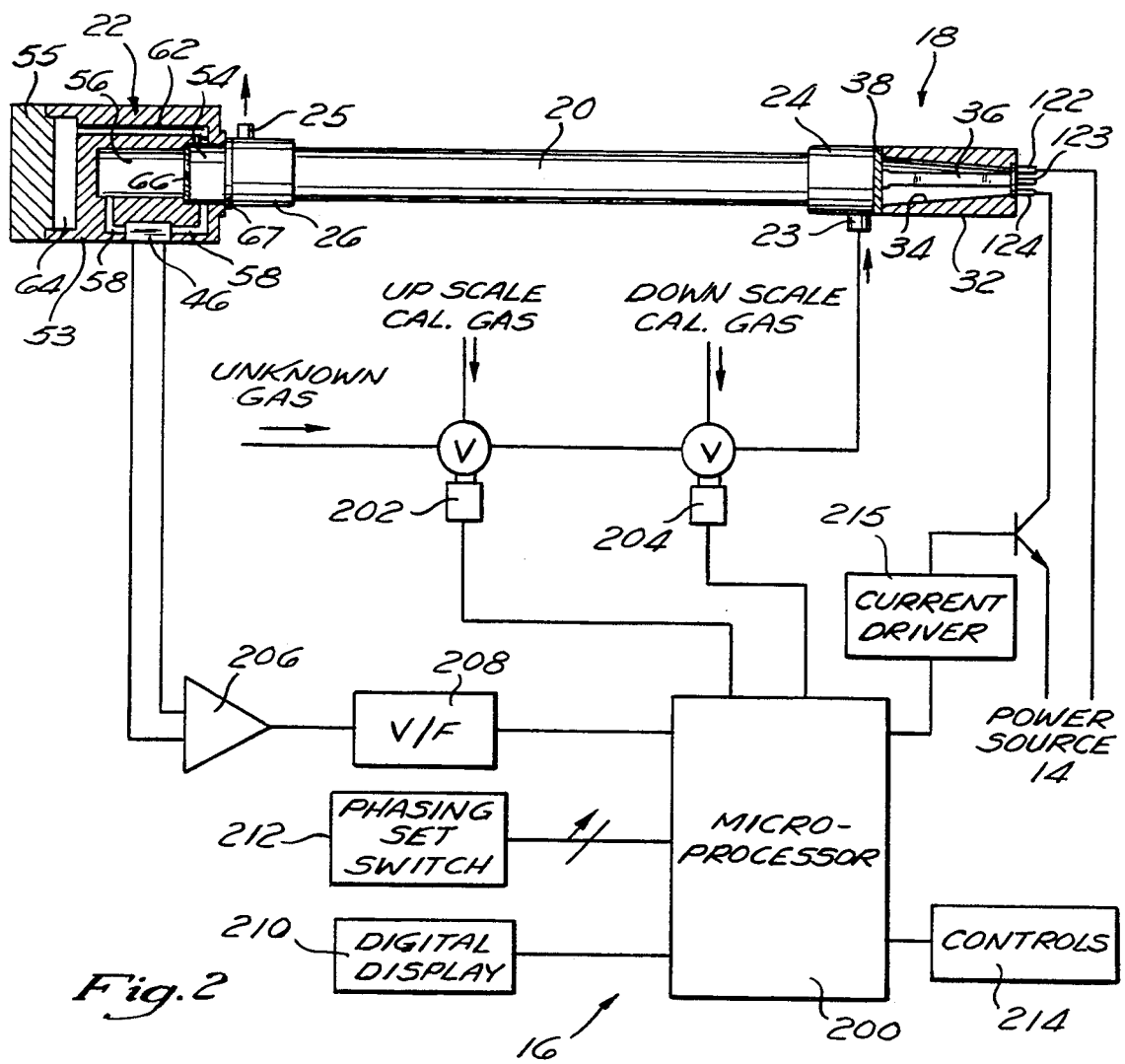
FIG. 2 is a schematic representation of the electrical components of the infrared gas mixture analyzer of FIG. 1 showing their interconnection with the infrared source and detector.

The infrared analyzer of the present invention is illustrated in FIG. 1 which depicts a presently preferred embodiment of the invention. The infrared analyzer is comprised generally of a housing or chassis 10 having a control panel 12 formed upon the front surface thereof and containing a power supply 14, processing and control electronics 16, infrared source 18, sample tube or cell 20, and infrared detector 22. Also contained (but not illustrated in FIG. 1) within the chassis 10 is conventional plumbing for introduction of a gas to be analyzed into the sample cell 20. As shown, the infrared source 18 is positioned upon a first end of the sample cell 20 and the infrared detector 22 is disposed upon a second end thereof such that infrared radiation from the source 18 passes through the gas to be analyzed contained within the sample cell 20 and subsequently into the infrared detector 22. As will be explained in more detail infra, the infrared detector 22 defines a front detection cell or chamber 54, a rear detection cell or chamber 56, and an auxiliary or balancing chamber 64. An interconnecting conduit 58 extends between the front and rear detection cells 54 and 56, respectively, and a mass flow sensor 46 is disposed therein. The mass flow sensor 46 is electrically connected to the processing and control electronics 16 (as illustrated in FIG. 2).

As a basic overview, analysis of an unknown gas is accomplished by passing a sample of the unknown gas through the sample cell 20 while pulsing the infrared radiation source 18 such that a portion of the infrared radiation emitted therefrom is absorbed by the gas being analyzed contained within sample cell 20 and a further portion of the infrared radiation is transmitted therethrough to detector 22. A portion of the infrared radiation entering detector 22 is absorbed by the gas contained within front detection cell 54 while a further portion thereof is transmitted through front detection cell 54 into rear detection cell 56 where a further portion thereof is absorbed by the gas contained therein.

The absorption of infrared radiation by the diluent gases contained within the front 54 and rear 56 detection cells causes expansion of the gases contained therein, resulting in flow through the interconnecting conduit 58. The flow of gas through the interconnecting conduit 58 is measured by mass flow sensor 46. The output of mass flow sensor 46 is inversely proportional to the quantity of a dipole gas contained within sample cell 20 since increased concentrations of the dipole gas within the sample cell 20 result in increased absorption of infrared radiation thereby, consequently resulting in reduced absorption of the infrared radiation within the detector 22. The output from the sensor 46 is processed by the processing and control electronics 16 and a resultant output of the concentration of the gas of interest contained within the sample cell 20 is provided.

With this broad operational overview, a detailed description of the construction of each of the major components of the infrared analyzer follows.

SAMPLE CELL

As best shown in FIGS. 1 and 2, the sample cell 20 of the present invention is disposed between and optically coupled to the infrared radiation source 18 and infrared detector 22. The sample cell 20 is preferably fabricated as an elongate glass or silica tube typically having an inside diameter ranging between 1.27 centimeters (one-half inch) and 2.54 centimeters (one inch). The interior annular wall of the sample cell 20 is preferably coated with a thin film of gold to minimize the absorption of infrared radiation by the wall of the sample cell 20. The gold coating provides an infrared reflective surface which tends to keep the infrared radiation emanating from the source 18 within the sample cell 20 and thereby improves the efficiency and sensitivity of the infrared analyzer.

Preferably the gold coating is applied as a gold salt to the inner annular surface of the sample cell 20 to reside thereon and subsequently the sample cell 20 is heated to a temperature generally commensurate with the softening point of the glass or silica material of the sample cell. During this heating process, an internal infrared reflective gold film is fused thereon. One example of a gold salt suitable for such use is Liquid Bright Gold, a product of Engelhard of East Newark, N.J. As will be recognized, by such a coating procedure, costly prior art hand polishing of the interior of the sample cell is avoided.

Opposite ends of the sample cell 20 are fitted with a pair of end caps 24 and 26, preferably formed of a thermoplastic material. The sample cell end caps employ "O" rings to effect a gas-tight seal. Preferably, sapphire or $CaF_2$ windows seal the cell and transmit infrared energy therethrough- The distal ends of both end caps 24 and 26 additionally include an aperture having a diameter equal to or slightly greater than the inside diameter of the sample cell 20, such that radiation emitted by the infrared radiation source 18 is permitted to travel through the interior of the sample cell 20 to the infrared detector 22. An inlet port 23 and outlet port 25 is additionally provided on the end caps 24 and 26, respectively, which enables a quantity of gas desired to be analyzed to be introduced into the interior of the sample cell 20.

INFRARED RADIATION SOURCE

Figure 11:
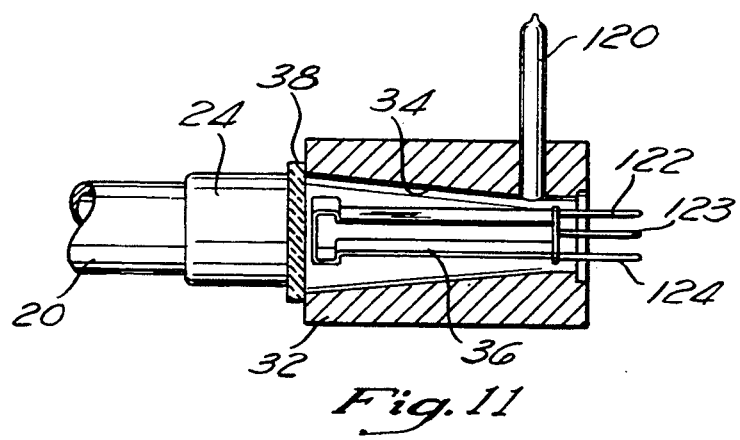
FIG. 11 is a cross-sectional side view of the infrared source of the present invention.

Referring more particularly to FIGS. 2 and 11, the infrared source 18 of the present invention preferably comprises a housing 32 having a generally V-shaped infrared reflective interior 34. A foil element 36 is disposed within the interior 34 which is electrically connected to electrode contacts 122, 123, and 124, such that an electrical current may be applied thereto. The foil element 36 preferably includes a low thermal mass and a large radiation area. The proximal end of the housing 32 is provided with an infrared transmissive window 38 which is sealed thereto and which is additionally adapted to provide an optical interface between the radiation source 18 and end cap 24 of the sample cell 20. In the preferred embodiment, the window 38 is formed of a sapphire material, however other infrared transmissive materials are contemplated herein. As shown in FIG. 11, the housing 32 additionally is preferably provided with a sealable evacuation tube 120 which facilitates evacuation of the interior of the housing 32 and/or the filling of the interior of the housing 32 with desired gases.

The foil element 36 is preferably formed to have a thickness of less than 0.0005 centimeters (0.0002 inch) and may be formed of differing materials as desired. In the preferred embodiment, two alternative materials are contemplated, i.e., a nickel aluminum alloy and a platinum tungsten alloy. A nickel aluminum alloy, known as KANTHAL (a registered trademark of the Kanthal Corporation of Stanford, Conn., is a preferred material candidate. When using such a nickel alloy, such as KANTHAL alloy material, the interior 34 of the housing 32 is preferably evacuated by drawing a hard vacuum through tube 120. Additionally, such hard vacuum is facilitated in the presence of a suitable desiccant, such as a $P_2O_5$ desiccant to scavenge any residual water vapor from the interior of the housing 32. Subsequently, the tube 120 is sealed to maintain a water-free and air-free environment within the interior of the housing 32. In such applications, the sapphire window 38 is additionally provided with a conventional filter coating which serves to eliminate, i.e. block, any water signal traveling through the window 38 and into the interior of the sample cell 20.

Alternatively, a preferred material candidate for the foil element 36 comprises a platinum tungsten alloy containing approximately 10 percent tungsten. Preferably the tungsten foil is coated with a thin layer of nickel which is applied by conventional sputtering onto the foil. The nickel coating is then oxidized to produce a surface possessing good black body emission characteristics in the infrared emission spectrum.

The interior of the infrared radiation source may additionally be charged with an interfering gas, i.e. a dipole gas which is expected to be present in the unknown gas mixture within the sample cell 20 and the quantity of which is not desired to be known. Such charging is facilitated by first drawing a vacuum through tube 120 and subsequently introducing a quantity of such gas back through tube 120 and sealing the same. As will be recognized, due to the heat generated by the foil element 36 during operation, the source prevents condensation of the interfering gas on the inner walls of the source, thereby allowing high concentration of gases having relatively condensation temperatures to be utilized.

INFRARED DETECTOR

Referring now to FIGS. 2 and 3, the infrared detector 22 is formed from a pair of housing segments 53 and 55, preferably fabricated from a brass material. A pair of annular apertures define the front detection cell or chamber 54 and rear detection cell or chamber 56. The housing segment 55 includes an annular shoulder 57 which may be slidingly received within a complimentary shaped recess 59 formed within the housing segment 55. The cavity formed by the recess 59 and housing segment 55 defines the auxiliary or balancing chamber 64, the volumetric size of which may be varied depending upon the axial insertion of the annular shoulder 57 within the annular recess 59. As will be explained in more detail infra, the particular volumetric sizing of the auxiliary or balancing chamber 64 is determined empirically for the particular sensor to balance the signals received from the front 54 and rear 56 chambers.

An infrared transparent window 55, preferably formed of sapphire, seals the outermost opening of the front detection cell 54 and cooperates with the end cap 26 to form an optical interface between the infrared detector 22 and the sample cell 20. Similarly, an infrared transparent window 66, preferably formed of sapphire, seals the outer opening of the rear detection cell 56 and forms the optical interface between the front 54 and rear 56 detection cells within the housing segment 53. An internal flow channel or conduit 62 is formed within the housing segment 53 and provides a flow path between the front detection cell 54 and auxiliary or balancing chamber 64. In this regard, it will be recognized that the volume of the conduit 62 forms a portion of the overall volume of the balancing chamber 64. Similarly, an internal flow channel or conduit 58 is provided within the interior of the housing segment 53 which provides a gas flow path between the front detection cell 54 and rear detection cell 56. An enlarged cavity 61 is additionally provided within the conduit 58 in which is disposed the mass flow sensor 46 of the present invention.

A diluent gas, preferably comprising a xenon gas, is preferably provided within the front and rear detection cells 54 and 56, respectively. Additionally, a known quantity of a sensitizing gas, having substantially similar absorption spectra to that of the gas being analyzed, is preferably mixed with the diluent gas. When desired, an infrared baffle 60 may additionally be disposed within the conduit 62 which prevents the undesirable transmission of infrared radiation from the front detection cell 56 to the balancing reservoir 64 but does not impede gas flow within the conduit 58.

Although not by way of limitation, in the preferred embodiment a xenon gas is utilized as the diluent gas which includes a known quantity of sensitizing gas to effect expansion thereof due to absorption of infrared radiation from the radiation source 18. The sensitizing gas preferably includes a similar infrared absorption spectrum to that of the gas desired to be analyzed in the sample cell 20. This permits the use of filters to identify the particular absorption spectra of the unknown gas and thereby determine its identity. That is, the sensitizing gas should have a similar absorption spectra to that of the gas being analyzed such that it is responsive to the same frequencies of infrared radiation, thereby improving the sensitivity of the infrared analyzer.

In the preferred embodiment, xenon is preferably utilized as the diluent gas because of its superior thermal conduction and specific heat properties, as previously listed in the table of principal diluent gases.

MASS FLOW SENSOR

The mass flow sensor of the present invention is depicted generally in FIGS. 4–10 and in the preferred embodiment comprises a dual-resistive heating element type sensor. Referring more particularly to FIG. 4, the sensor 46 is preferably formed having a pair of support members 98 and 99, each of which is provided with plural mounting apertures 100 and a square aperture 108 formed centrally therethrough. Although such housing members 98 and 99 may be formed of glass or anodized aluminum, in the preferred embodiment the same are fabricated from a polymer via an injection molding process.

Figure 10:
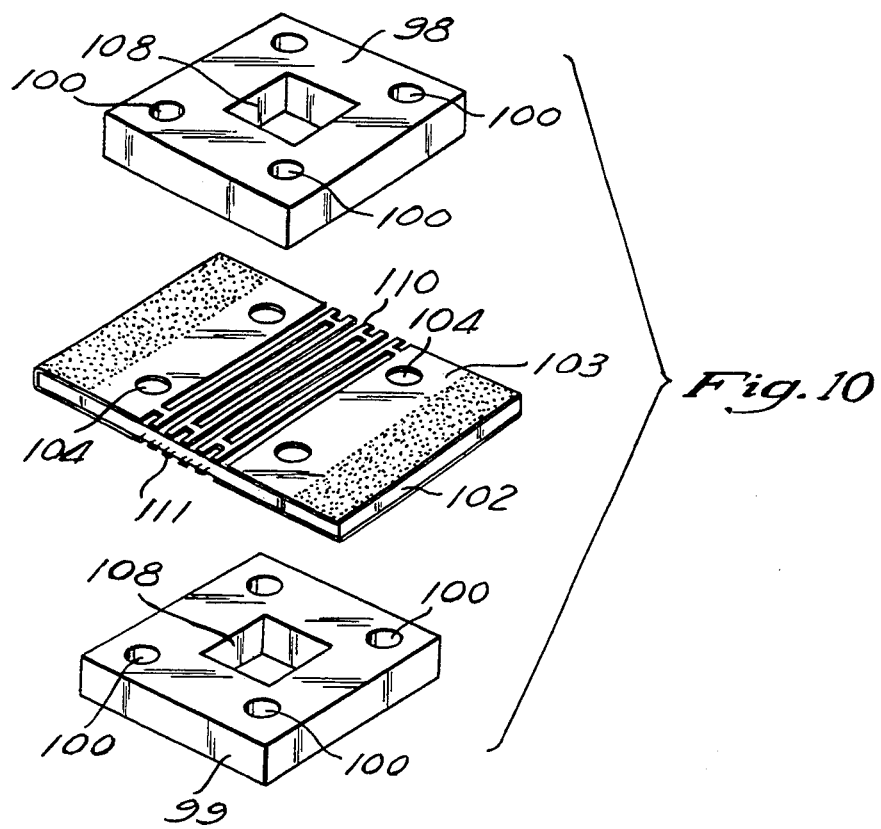
FIG. 10 is an exploded perspective view of the mass flow sensor.

The support members 98 and 99 carry or support a pair of resistive heating elements 110 and 111 which, as best depicted in FIG. 7, are disposed in an overlying relationship with one another and separated by an insulating plate 102. In the preferred embodiment, the insulating plate 102 is formed from glass and comprises an electrical insulator and additionally includes a plurality of mounting apertures 104 and a central square aperture 106. The resistive heating elements 110 and 111 are disposed on opposite sides of the insulating plate 102 and are positioned to extend over the square aperture 106 formed in the insulating plate 102, as best shown in FIG. 10.

When assembled, the support plates 98 and 99 are positioned on opposite sides of the insulating plate 102 having the resistive elements 110 and 111 extending thereover and are secured together in a sandwich-like configuration wherein the square apertures 108, formed in both of the support members 98 and 99, are axially aligned with the square aperture 106 formed in the insulating plate 102. In such a sandwiched assembly, the plural apertures 100 formed in the support members 98 and 99 are axially aligned with the plural apertures 104 formed in the insulating plate 102 and facilitate mounting of the resultant sensor 64 within the cavity formed within the housing segment 53 of the infrared detector such that the resistive heating elements 110 and 111 are disposed within the flow cavity or channel 58 extending between the front detection cell 54 and rear detection cell 56.

The heating elements 110 and 111 are connected in opposite sides of a Wheatstone bridge. Gas flow cools the front heating element. The hot gas from the front heating element is moved to the rear heating element, warming it. Because these elements are selected to have a large coefficient of resistance with temperature change, the bridge balance is changed to produce an electrical signal.

Although differing methods are contemplated for forming the resistive heating elements 110 and 111, in the preferred embodiment of the present invention, the resistive heating elements 110 and 111 are formed in a novel process which insures production accuracy and reduces production costs. The process is illustrated in FIGS. 5 through 7. Referring to FIG. 5, the pair of resistive heating elements 110 and 111 are preferably formed from an elongate strip of titanium having an approximate thickness of 0.00056 centimeters (0.00022 inch) and a width of approximately 0.635 centimeters (0.25 inch). The titanium strip 103 is preferably formed having two pairs of plural apertures 105 extending therethrough on opposite ends thereof, the relative spacing of which is commensurate with the relative spacing of the plural apertures 100 formed in the support members 98 and 99 and plural apertures 104 formed in the insulating plate 102. The resistive heating elements 110 and 111 preferably are formed as plural elongate ultra-thin wires or wire portions upon the titanium strip 103 which extend transversely across the titanium strip 103 as shown.

In the preferred embodiment, the plural elongate wires 110 and 111 are fabricated utilizing a photo-etching process wherein the titanium plate is photo-etched to remove the portions of the titanium strip existing between selected portions of the plural elongate wires. Due to the extreme thinness of the titanium strip 103, the photo-etching process is preferably accomplished to leave opposite end portions of the plural wires 111 connected, as depicted in FIG. 5. In order to allow conventional silver solder techniques to be employed to make electrical connections to the heating elements 110 and 111, the end and central portions of the titanium strip 103 are preferably coated with chromium, nickel, and copper layer as depicted by the shaded portions in FIGS. 5 and 7. In the preferred embodiment, the chromium, nickel, and copper are sequentially applied by conventional sputtering techniques such that a thin layer of chromium followed by a thin layer of nickel followed by a thin layer of copper is applied to the central and end portions of the titanium strip 103. As will be recognized, the chromium layer forms a strong bond to titanium, while the nickel layer additionally forms a strong bond to the chromium. The copper layer is utilized to form a bond to the nickel layer and additionally prevent nickel oxide development during the silver soldering process.

Subsequently, the titanium strip 103 is trimmed, as by way of a knife, to remove the end connection portions of the plural wires 110 and 111 as depicted in FIG. 6, with the phantom lines in FIG. 6 depicting the removed cutaway portion of the titanium strip. As further depicted in FIG. 6, the resultant plural elongate wires after trimming define a series flow path between the elongate wires or grid, thereby forming a pair of titanium grid resistive heating elements 110 and 111 upon the titanium strip.

Following formation of the titanium strip in the manner aforesaid, the titanium strip 103 is folded about itself, as illustrated in FIG. 7, with the insulating plate 102 being disposed between the heater elements 110 and 111. Subsequently, the support members 98 and 99 may be affixed on opposite sides of the heater element and suitable electric lead connections to the titanium strip 103 may be facilitated. As best shown in FIG. 4, the electrical connections typically comprise a pair of separate lead connections 121 and 123, which are applied to the distal end portions of the titanium strip 103 and a common electrical lead connection 125 connected to the central portion of the titanium strip 103.

PROCESSING AND CONTROL ELECTRONICS

The operating sequence and functions of operation of the analyzer of the present invention is controlled by the processing and control electronics 16. As best shown in FIG. 2, the control and processing electronics 16 includes a microprocessor 200 which includes in storage, a sequence of commands to effectuate the control and operation of the analyzer. The microprocessor is connected to a power source 14 and further drives a chopped current driver which provides current to the infrared radiation source 18. The microprocessor additionally controls the operation of a pair of valves 202 and 204, the operation of which causes a quantity of calibrant gas to be selectively introduced within the interior of the sample cell 20, as well as a quantity of unknown gas desired to be analyzed. The output of the mass flow sensor 46 is amplified via amplifier 206 to a desired level to boost the same to a suitable level. Subsequently, a voltage-to-frequency converter 208 is utilized to provide an analog-to-digital conversion. The output from the voltage-to-frequency converter 208 is provided to the circuit counter of the microprocessor 200 which counts the pulses for the positive half of the source signal and subtracts the signal during the second half. The difference is a measure of an integrated signal during the cycle which is equivalent of an analog-to-digital conversion with 16-place accuracy. The integrated reading is then used as a new value for providing a current update for every cycle. Where fast response is not required, a weighted averaging is employed to remove the noise at the expense of speed response. The process output may then be utilized in conjunction with look-up tables stored within the memory of the microprocessor, the appropriate values of which may then be displayed on the digital display 210. In the preferred embodiment, a phase-setting switch 212 is additionally provided, and suitable controls 214 communicate with the microprocessor 200. As will be recognized, the particular phase-setting switch, digital display, and controls to the microprocessor 200 are preferably implemented as components mounted on the front wall of the analyzer housing 12.

DETAILED OPERATION OF THE INFRARED ANALYZER

The irradiation source 18 is activated, causing a pulsed radiation beam to be emitted from the infrared source 18 to travel through the interior of the sample cell 20, and into the front and rear detection cells 54 and 56 of the detector 22. The unknown gas in the sample cell 20 absorbs energy from this beam at wavelengths dependent on its composition and concentration. The sensitizing gas in the detector cell is chosen to have absorption at the same wavelengths as the analyte. The energy reaching the detector from the sample cell at these wavelengths is a function of the concentration of analyte in the sample cell 20. Most of the energy at these analyte wavelengths is absorbed by the front detector chamber 54. The remaining is absorbed by the rear chamber 56.

In previous detectors of this type the resulting signal from the front chamber is stronger. For analyzers where the analyte is present in trace amounts the full scale concentrations typically produce 4 percent to 5 percent change in the detector signal. Under these conditions, slight changes in source emission, sample cell optical transmission, etc. results in a major error in the reported concentration. The balancing chamber 64 increases the flow from the rear chamber 56 by reducing the pressure buildup resulting from this flow. The size of this balancing chamber 64 is selected so that signals from the front 54 and rear 56 chambers approximately cancel and the resulting detector signal change is large for trace gases. Therefore the effects of changes in source 18 and sample cell 20 are greatly reduced. For the preferred balance the detector signal goes through zero resulting in a 180-degree phase shift requiring synchronous detection.

To facilitate an actual measurement or analysis of an unknown gas, the infrared analyzer is initially calibrated by a 2-point or step calibration process. This calibration process preferably comprises the initial introduction of a gas having a zero concentration of the analyte. The microprocessor sets the counts received under these conditions in its memory to equal zero concentration. A second, similar calibration process is then repeated for upscale concentration of the calibrant gas.

Subsequently, to perform analysis of an unknown gas, a quantity of unknown gas is introduced into sample cell 20 via opening of valves 202 and 204 under the control of microprocessor 78.

The infrared radiation source 18 is pulsed by supplying a pulsed trigger signal to switching current driver 214 by microprocessor 78. This facilitates pulse current flow through foil element 36 of the infrared radiation source 18. The application of pulsed current to the foil element 36 of the infrared radiation source 18 causes the foil element 36 to alternately heat up and cool down such that pulsed infrared radiation is radiated through the infrared transmissive window 38 and into sample cell 20.

As discussed above, a portion of the infrared radiation from infrared radiation source 18 is absorbed by any dipole gases present within sample cell 20 and a further portion of the infrared radiation is transmitted therethrough the detector 22. That portion of the infrared radiation not absorbed by dipole gases contained within the sample cell 20 is transmitted through infrared transmissive window 55 into front detection cell 54. A portion of the infrared radiation entering front detection cell 54 is absorbed by the sensitizing gas contained therein and a further portion of the infrared radiation is transmitted through infrared transmissive window 53 to rear detection cell 56.

The absorption of infrared radiation by the sensitizing gas contained within front detection cell 54 and rear detection cell 56 results in expansion thereof and consequently results in a gas flow through interconnecting conduits 58. The gas flow through the interconnecting conduit 58 additionally flows through the square apertures 106 and 108 formed within the mass flow sensor 46 in either a direction from the rear detection cell 56 toward the front detection cell 54 or alternatively from the front detection cell 54 to the rear detection cell 56. The resistive heating elements 110 and 111 of the mass flow detector 46 are connected in a Wheatstone bridge circuit and a heating current is supplied to the bridge. During gas flow across the mass flow detector 46, a selective cooling of the resisting heating elements 110 and 111 occurs, with the particular heating element being first contacted by the direction of gas flow across the sensor being cooled to a greater extent than the subsequent heating element. Due to the high temperature coefficient of the elements, a signal is generated across the galvanometer branch of the bridge which is proportional to the amount of gas flow across the sensor 46.

Where fast response is desired with conventional detection systems it is necessary to chop the source at a high frequency since the rectified signal must be filtered to remove the pulsations from the signal. Since the infrared radiation detector has poor frequency response, a compromise between system response time and signal-to-noise is necessary. In the infrared analyzer of the present invention, this compromise is greatly reduced because the voltage-to-frequency circuit integrates the signal during each cycle. This provides a new point and does not require the smoothing actions of low pass filters as employed in contemporary systems.

The output of the voltage-to-frequency converter 72 is a sine-like varying frequency signal. That is, the frequency increases and decreases periodically about a center frequency, thus defining a sine-like waveform. To obtain a value representative of the flow of gas through the mass flow sensor 46, it is necessary to subtract the lower portion of the sine-like wave form from the upper portion thereof, or vice versa. To do this, the microprocessor counts the pulses for the positive half of the source signal and then subtracts the counts during the lower or second half. This difference is a measure of the magnitude of the integrated signal during the cycle with the equivalent of an A-D converter with 16-place accuracy. This integrated reading can be used as a new value providing a current update every cycle.

When fast response is not required, a weighted averaging is employed to improve the noise at the expense of the speed of the response. A reduction of this compromise is obtained by varying the weighting according to the magnitude of the change. For example, if the change is greater than 25 percent of the full scale, then no averaging is employed and if the change is less than one percent of full scale, then a maximum weighting is utilized. The synchronous counting circuit provides proper operation when used with the balance detector as the sign of the difference count changes when the signal goes through zero. This would not be true with straight rectification. The signal to noise is also improved since non-synchronous signals are attenuated.

The microprocessor 200 subsequently utilizes the processed output via a look-up table or polynomial equation having the corresponding particular concentration of the gas desired to be analyzed stored therein or defined thereby. The particular concentration value is then output by the microprocessor to the digital display 210. As will be recognized, in lieu of or simultaneous with the output to the digital display 210, the output of the microprocessor may be recorded by conventional techniques. The output of the frequency counter is provided to microprocessor 78 and is representative of the concentration of dipole gas contained within sample cell 20.

The signal supplied by mass flow sensor 46 is amplified by amplifier 206 and input to voltage-to-frequency converter 72 and then to a frequency counter internal to the microprocessor 78. The counts are added during the first half of the energy cycle and subtracted during the second half of the cycle. The microprocessor has a time delay counter started by the signal to the source current driver 214. The delay time is controlled by the phase set switch 212 and the delayed signal is used to control the timing of the add/subtract decisions. This difference count is a function of the absorbance of the analyte in the sample cell.

As will be recognized, any build-up of pressure within the front detection cell 54 which would inhibit the flow of gas from the rear detection cell 56 through interconnecting conduit 58 and which would thereby decrease the sensitivity of the detector 22 is avoided by the increased volume of the balancing chamber 64 which allows substantially unrestricted flow of gas from the rear detection cell 56 to the front detection cell 54.

It is understood that the exemplary infrared analyzer described herein and shown in the drawings represents only a presently preferred embodiment of the invention. Indeed, various modifications and additions may be made to such embodiment without departing from the spirit and scope of the invention. For example, the source, sample cell, and detection cell need not be configured as illustrated. Those skilled in the art will recognize that various other physical or optical configurations are equivalent and therefore likewise suitable. Thus, these and other modifications and additions may be obvious to those skilled in the art and may be implemented to adapt the present invention for use in a variety of different applications.

What is claimed is:

1. A detector for an infrared gas analyzer, said detector comprising:

(a) a front detection cell for receiving infrared radiation;

(b) a rear detection cell for receiving infrared radiation from said front detection cell;

(c) a gas flow sensor communicating with said front and rear detection cells; and (d) an auxiliary chamber in fluid communication with said front detection cell.

2. The detector as recited in claim 1 wherein the optical path of said front detection cell is shorter than the optical path of said rear detection cell.

3. The detector as recited in claim 1 further comprising an infrared radiation baffle disposed intermediate said front detection cell and said auxiliary chamber such that the transmission of infrared radiation from said front detection cell to said auxiliary chamber is substantially mitigated.

4. The detector as recited in claim 1 wherein the auxiliary chamber has a volume selected to approximately balance the signals from the front and back cells.

5. The detector as recited in claim 4 further comprising a sensitizing gas mixed with xenon gas, said sensitizing gas having a substantially similar infrared absorption spectra to that of a gas being analyzed.

6. A detector for an infrared analyzer, said detector comprising:

(a) a front detection cell receiving infrared radiation;

(b) a rear detection cell receiving infrared radiation from said front detection cell; and (c) a flow sensor fluidly connected between said front and rear detector cells; and (d) xenon gas mixed with a sensitizing gas having substantially similar infrared absorption spectra to that of a gas being analyzed disposed within said front and rear detection cells.

7. An infrared analyzer comprising:

a) a sample cell for containing a sample gas to be analyzed;

b) a pulsed infrared radiation source disposed adjacent one end of said sample cell;

c) a detector disposed adjacent the opposite end of said sample cell for measuring the infrared radiation radiated through said sample chamber, said detector comprising:

i) a front detection cell receiving infrared radiation;

ii) a rear detection cell receiving infrared radiation from said front detection cell; and iii) a balancing chamber in fluid communication with said front detection cell for controlling expansion of gas within said front detection cell; and d) a linearization circuit for linearizing the output of said detector such that an output of the linearization circuit corresponds to the concentration of a desired gas in the sample gas, said linearization circuit comprising:

i) a voltage-to-frequency converter;

ii) a look-up table containing concentration values corresponding to detector outputs; and iii) a microprocessor for looking up the concentration in said look-up table corresponding to an output of said detector.

8. An infrared analyzer comprising:

(a) a sample cell for containing a sample gas to be analyzed;

(b) a infrared radiation source: and (c) a detector for measuring the infrared radiation radiated through said sample cell, said detector comprising:

(i) a front detection cell receiving infrared radiation;

(ii) a rear detection cell receiving infrared radiation from said front detection cell; and (iii) a flow sensor fluidly connected between said front and rear chambers, an auxiliary chamber fluidly connected with said front chamber, said auxiliary chamber's volume selected to approximately balance the flow signals produced by said front and rear chambers and sensed by said flow sensor.

9. The infrared analyzer as recited in claim 8 wherein said infrared radiation source comprises an infrared radiation source configured for pulsed operation, and further comprising an amplifier to amplify the signals received from said flow sensor, said signals defining a cycle due to reversal of gas flow within said flow sensor, a voltage-to-frequency converter circuit receiving the output from said amplifier, a counter circuit connected to the output from said voltage-to-frequency circuit, said counter counting the output of said voltage-to-frequency circuit during both a first half of the cycle and a second half of the cycle, the counts during the second half of said cycle being subtracted from the counts during the first half thereof, the difference being representative of the concentration of an analyte.

10. The infrared analyzer as recited in claim 9 further comprising a signal synchronous with the pulsed operation, an adjustable timed delay circuit connected to said synchronous signal, the output from said timed delay circuit employed to determine the timing of the count addition and subtraction of said counter.

11. The infrared analyzer as recited in claim 10 wherein said timed delay circuit comprises a microprocessor having a digital input to select the delay time.

12. The infrared analyzer as recited in claim 10 further comprising a microprocessor for generating a polynomial equation to convert the counts to an output linear with the concentration of an analyte.

13. The infrared analyzer as recited in claim 10 further comprising a microprocessor for utilizing a lookup table to convert the counts to an output linear with concentration of the analyte.

14. An infrared analyzer comprising:

a) a sample cell for containing a sample gas to be analyzed;

b) a pulsed infrared radiation source disposed adjacent one end of said sample cell;

c) a detector disposed adjacent the opposite end of said sample cell for measuring the infrared radiation radiated through said sample chamber, said detector comprising:

i) a front detection cell receiving infrared radiation;

ii) a rear detection cell receiving infrared radiation from said front detection cell; and iii) a balancing chamber in fluid communication with said front detection cell for controlling expansion of gas within said front detection cell; and d) a linearization circuit for linearizing the output of said detector such that an output of the linearization circuit corresponds to the concentration of a desired gas in the sample gas, said linearization circuit comprising a linearization means for defining a polynomial which relates detector outputs to concentrations of a gas being analyzed.

* * * * *